(12) United States Patent
Orser et al.

(10) Patent No.: US 7,166,471 B2
(45) Date of Patent: Jan. 23, 2007

(54) MISFOLDED PROTEIN SENSOR METHOD IN BODY FLUIDS

(75) Inventors: Cindy Orser, McLean, VA (US); Anne Grosset, La Croix-de-Rozon (CH); Eugene A Davidson, Washington, DC (US)

(73) Assignee: Arete Associates, Sherman Oaks, CA (US)

( * ) Notice: Subject to any disclaimer, the term of this patent is extended or adjusted under 35 U.S.C. 154(b) by 196 days.

(21) Appl. No.: 10/161,061

(22) Filed: May 30, 2002

(65) Prior Publication Data

US 2003/0104633 A1 Jun. 5, 2003

Related U.S. Application Data

(60) Provisional application No. 60/295,456, filed on May 31, 2001.

(51) Int. Cl.
*G01N 33/00* (2006.01)
(52) U.S. Cl. .......................... 436/86; 530/350
(58) Field of Classification Search .............. 436/86; 530/350
See application file for complete search history.

(56) References Cited

U.S. PATENT DOCUMENTS

| 5,977,324 | A * | 11/1999 | Prusiner et al. | 530/418 |
|---|---|---|---|---|
| 6,214,565 | B1 * | 4/2001 | Prusiner et al. | 435/7.1 |
| 6,399,314 | B1 * | 6/2002 | Krishnamurthy | 435/7.1 |
| 6,677,125 | B1 * | 1/2004 | Prusiner et al. | 435/7.1 |
| 6,750,025 | B1 * | 6/2004 | Hammond et al. | 435/7.1 |
| 2001/0001061 | A1 | 5/2001 | Safar et al. | |
| 2002/0042121 | A1 | 4/2002 | Riesner et al. | |
| 2003/0215880 | A1 | 11/2003 | Burton et al. | |
| 2005/0112607 | A1 * | 5/2005 | Bamdad et al. | 435/6 |

FOREIGN PATENT DOCUMENTS

| WO | WO 97/43649 | 11/1997 |
|---|---|---|
| WO | WO 00/02575 | 1/2000 |
| WO | WO 00/43791 | 7/2000 |
| WO | WO 01 07473 A | 2/2001 |
| WO | WO 01 14412 A | 3/2001 |
| WO | WO 03/085086 | 10/2003 |

(Continued)

OTHER PUBLICATIONS

Pan et al. "Conversion of alpha-helices into beta-sheets features in the formation of the scrapie prion proteins," Proc. of National Academy of Science, USA, vol. 90, pp. 10962-10966, (1993).*

(Continued)

*Primary Examiner*—Monique T. Cole
(74) *Attorney, Agent, or Firm*—Foley & Lardner LLP

(57) ABSTRACT

A catalytic conformational sensor method for detecting abnormal proteins and proteinaceous particles. The method is based on the interaction of a peptide fragment or probe with an abnormal proteinaceous particle. The interaction catalyzes transformation of the probe to a predominately beta sheet conformation and allows the probe to bind to the abnormal proteinaceous particle. This in turn, catalyzes propagation of a signal associated with the test sample-bound probe. As a result signals can be propagated even from samples containing very low concentrations of abnormal proteinaceous particles as is the case in many body-fluid derived samples.

36 Claims, 7 Drawing Sheets

FOREIGN PATENT DOCUMENTS

WO    WO 2004/018511    3/2004

OTHER PUBLICATIONS

Shaked et al. "A Protease-resistant Prion Protein Isoform is Present in Urine of Animals & Humans Affected with Prion Diseases," Journal of Biological Chemistry, vol. 276, No. 34, pp. 31479-31482, 2001.*

Anantharamaiah, G.M., et al., "Studies of Synthetic Peptide Analogs of the Amphipathic Helix", *J. Biol. Chem.* 260(18):10248-10255, 1985.

Anfinsen, C.B., "Principles that Govern the Folding of Protein Chains", *Science* 181(4096):223-230, 1973.

Baba, M., et al., "Aggregation of α-Synuclein in Lewy Bodies of Sporadic Parkinson's Disease and Dementia with Lewy Bodies", *Am. J. Patthology* 152(4):879-885, 1998.

Baker, D., "A surprising simplicity to protein folding", *Nature* 405:39-42, 2000.

Booth, D.R., et al., "Instability, unfolding and aggregation of human lysozyme variants underlying amyloid fibrillogenesis", *Nature* 385:787-793, 1997.

Carrell, R.W. et al., "Conformational Disease", *The Lancet* 350:134-138, 1997.

Chiti, F., et al., "Designing conditions for *in vitro* formation of amyloid protofilaments and fibrils", *Proc. Natl. Acad. Sci. USA* 96:3590-3594, 1999.

Daura, X., et al., "Reversible Peptide Folding in Solution by Molecular Dynamics Simulation", *J. Mol. Biol.* 280:925-932, 1998.

Dobson, C.M., "The structural basis of protein folding and its links with human disease", *Phil. Trans. R. Soc. London B* 356:133-145, 2001.

Dobson, C.M. et al., "Kinetic studies of protein folding using NMR spectroscopy", *Nature Structural Biology* Suppl:504-507, Jul. 1998.

Epstein, F.H., "Molecular Basis Of The Neurodegenerative Disorders", *New. Eng. J. Med.* 340(25):1970-1980, 1999.

Isenman, D.E., et al., "The Structure and Function of Immunoglobulin Domains", *Proc. Natl. Acad. Sci. USA* 72(2):548-552, 1975.

Krawczak, M., et al., "Human Gene Mutation Database—A Biomedical Information and Research Resource", *Human Mutation* 15:45-51, 2000.

Lansbury, P.T., "Evolution of amyloid: What normal protein folding may tell us about fibrillogenesis and disease", *Proc. Natl. Acad. Sci. USA* 96:3342-3344, 1999.

Levy, E., et al., "Stroke In Icelandic Patients With Hereditary Amyloid Angiopathy Is Related To A Mutation In The Cystatin C Gene, An Inhibitor Of Cysteine Proteases", *J. Exp. Med.* 169:1771-1778, 1989.

Liao, Y-C.J., et al., "Human Prion Protein cDNA: Molecular Cloning, Chromosomal Mapping, and Biological Implications", *Science* 233:364-367, 1986.

MacPhee, C.E., et al., "Chemical Dissection and Reassembly of Amyloid Fibrils Formed by a Peptide Fragment of Transthyretin", *J. Mol. Biol.* 297:1203-1215, 2000.

Matouschek, A., et al., "Mapping the transition state and pathway of protein folding by protein engineering", *Nature* 340:122-126, 1989.

Nguyen, J., et al., "Prion Protein Peptides Induce α-Helix to β-Sheet Conformational Transitions", *Biochemistry* 34:4186-4192, 1995.

Oesch, B., et al., "A Cellular Gene Encodes Scrapie PrP 27-30 Protein", *Cell* 40:735-746, 1985.

Perutz, M.F., "Glutamine repeats and neurodegenerative disease: molecular aspects", *TIBS* 24:58-63, 1999.

Prusiner, S.B., et al., "Prion Protein Biology", *Cell* 93:337-348, 1998.

Riordan, J.R., "Identification of the Cystic Fibrosis Gene: Cloning and Characterization of Complementary DNA", *Science* 245:1066-1073, 1989.

Salmona, M., et al., "Molecular determinants of the physicochemical properties of a critical prion protein region comprising residues 106-126", *Biochemical Journal* 342:207-214, 1999.

Schatzl, H.M., "Prion Protein Gene Variation Among Primates", *J. Mol. Biol.* 245:362-374, 1995.

Soto, C., "Protein misfolding and disease; protein refolding and therapy", *FEBS Letters* 498:204-207, 2001.

Speed, M.A., et al., "Polymerization Mechanism of Polypeptide Chain Aggregation", *Biotechnology and Bioengineering* 54(4):333-343, 1997.

Speed, M.A,, et al., "Specific aggregation of partially folded polypeptide chains: The molecular basis of inclusion body composition", *Nature Biotechnology* 14:1283-1287, 1996.

Spillantini, M.G., "α-Synuclein in filamentous inclusions of Lewy bodies from Parkinson's disease and dementia with Lewy bodies", *Proc. Natl. Acad. Sci. USA* 95:6469-6473, 1998.

Spillantini, M.G., "α-Synuclein in Lewy bodies" *Nature* 388:839-840, 1997.

Stahl, N., et al., "Prions and prion proteins", *The FASEB Journal* 5:2799-2807, 1991.

Surewicz, W.K., et al., "Infrared spectroscopic evidence of conformational transitions of an atrial natriuretic peptide", *Proc. Natl. Acad. Sci. USA* 84:7028-7030, 1987.

Thomas, P.J., et al., "Defective protein folding as a basis of human disease", *TIBS* 20:456-459, 1995.

Westaway, D., et al., "Distinct Prion Proteins in Short and Long Scrapie Incubation Period Mice", *Cell* 51:651-662, 1987.

Prior, R., et al., "Selective binding of Soluble Aβ1 -40 and Aβ1 -42 to a Subset of Senile Plaques", *Am. J. Pathology* 148(6):1740-1756, 1996.

Chitnumsub et al. (1999) "The Nucleation of Monomeric Parallel Beta-Sheet-Like Structures and Their Self-Assembly in Aqueous Solution" *Biorganic & Medicinal Chemistry* 7 (1): 39-59.

Fraser et al. (1994) "Conformation and Fibrillogenesis of Alzheimer A-beta Peptides with Selected Substitution of Charged Residues" *Journal of Molecular Biology* 244 (1): 64-73.

Wilson et al. (2000) "Conformational Transitions in Model Silk Peptides" *Biophysical Journal* 78 (5): 2690-2701.

* cited by examiner

| Temperature (°C) | 25 °C | 50 °C |
|---|---|---|
| pH 7 alone | Random coil | Random coil |
| pH 11 alone | alpha-helix | beta-sheet |
| pH 7 + pH 11 | beta-sheet | beta-sheet |
| pH 11 at 25 °C + pH 11 at 50 °C | Random coil | ---------- |

Figure 5

MISFOLDED PROTEIN SENSOR METHOD IN BODY FLUIDS

This document claims priority of U.S. provisional patent applications, Ser. No. 60/295,456 filed on May 31, 2001; which is hereby wholly incorporated by reference.

BACKGROUND

1. Field of the Invention

This invention relates generally to a catalytic conformational sensor method and application of such method for detecting proteins and proteinaceous particles; and more particularly to detecting misfolded or disease-associated proteins and proteinaceous particles.

2. Related Art

The present invention is not limited to the detection of proteins or peptides in infectious samples. It also includes detection of proteinaceous particles such as prions. Prions are small proteinaceous particles with no nucleic acids, thus are resistant to most nucleic-acid modifying procedures and proteases. They are infectious particles that play key roles in the transmission of several diseases such as Creutzfeldt-Jakob syndrome, transmissible spongiform encephalopathy (TSE), and scrapie a neurological disorder in sheep and goats. Diseases caused by prions can be hard to diagnose since the disease may be latent where the infection is dormant, or may be subclinical where abnormal prion is demonstrable but the disease remains an acute or chronic symptomless infection. Moreover, normal homologues of a prion-associated protein exist in the brains of uninfected organisms, further complicating detection.[2] Prions associate with a protein referred to as PrP 27-30, a 28 kdalton hydrophobic glycoprotein, that polymerizes (aggregates) into rod-like filaments, plaques of which are found in infected brains. The normal protein homologue differs from prions in that it is readily degradable as opposed to prions which are highly resistant to proteases. Some theorists believe that prions may contain extremely small amounts of highly infectious nucleic acid, undetectable by conventional assay methods.[3] As a result, many current techniques used to detect the presence of prion-related infections rely on the gross morphology changes in the brain and immunochemistry techniques that are generally applied only after symptoms have already manifest themselves.

[1] Clayton Thomas, *Tabor's Cyclopedic Medical Dictionary* (Phil., F.A. Davis Company, 1989), at 1485.
[2] Ivan Roitt, et al., *Immunology* (Mosby-Year Book Europe Limited, 1993), at 15.1.
[3] Benjamin Lewin, *Genes IV* (Oxford Univ. Press, New York, 1990), at 108.

The following is an evaluation of current detection methods.

Brain Tissue Sampling. Cross-sections of brain can be used to examine and monitor gross morphology changes indicative of disease states such as the appearance of spongiform in the brain, in addition to immunohistochemistry techniques such as antibody-based assays or affinity chromatography which can detect disease-specific prion deposits. These techniques are used for a conclusive bovine spongiform encephalopathy (BSE) diagnosis after slaughter of animals displaying clinical symptoms. Drawbacks of tissue sampling include belated detection that is possible only after symptoms appear, necessary slaughter of affected animals, and results that takes days to weeks to complete.

Prionic-Check also requires liquified-brain tissue for use with a novel antibody under the Western Blot technique. This test is as reliable as the immunochemistry technique and is more rapid, yielding results in six to seven hours, but shares the drawbacks of the six-month lag time between $PrP^S$ accumulation (responsible for the gross morphology changes) in the brain and the display of clinical symptoms, along with the need for slaughter of the animal to obtain a sample.

Tonsillar Biopsy Sampling. Though quite accurate, it requires surgical intervention and the requisite days to weeks to obtain results.

Body Fluids: Blood and Cerebrospinal Sampling. As in the above detection methods, results are not immediate Electrospray ionization mass spectrometry (ESI-MS), nuclear magnetic resonance NMR, circular dichroism (CD) and other non-amplified structural techniques. All of these techniques require a large amount of infectious sample, and have the disadvantage of requiring off-site testing or a large financial investment in equipment.

The difficulty with all of the presently approved tests is that they are time consuming and are performed POST-MORTEM.

As can now be seen, the related art remains subject to significant problems, and the efforts outlined above—although praiseworthy—have left room for considerable refinement. The present invention introduces such refinement.

SUMMARY OF THE DISCLOSURE

The present invention is based on the interaction between low concentration levels of abnormal proteinaceous particles and a peptide fragment or probe to induce transformation and propagation of the probe bound to the abnormal proteinaceous particles initially present within a test sample. Thus, in a preferred embodiment, infectious levels of a test sample can be propagated even from low concentrations as is the case in many body-fluid derived samples.

This invention overcomes many of the problems of prior art by using catalytic propagation to exploit conformational changes in proteins associated with a particular disease process, such as transmissible spongiform encephalopathy (TSE). Catalytic propagation basically amplifies the number of existing protein fragments causing aggregates to form. The aggregates of conformationally changed protein fragments are then easily detected using common analytical techniques. As a result, the present invention allows testing to be done using rapid and cost-effective analytical techniques, even on, heretofore difficult to detect, small sample sizes and is widely applicable to tissues and body fluids other than those found in brain. The invention is also relatively noninvasive in that it does not need to be performed post-mortem.

Moreover, results can easily and immediately interpreted using familiar analytical instrumentation. Additionally, the present invention can amplify a weak signal, thus can be successfully applied to small or weak samples such as those associated with body fluids; thereby opening the door to analysis of tissues and fluids for the elusive diseases discussed above.

All of the foregoing operational principles and advantages of the present invention will be more fully appreciated upon consideration of the following detailed description, with reference to the appended drawings, of which:

BRIEF DESCRIPTION OF THE DRAWINGS

FIG. 5 is a table comparing the circular dichroism results of the poly-L-lysine test peptide at different temperatures and pH;

DETAILED DESCRIPTION OF THE PREFERRED EMBODIMENTS

The present invention detects the presence of abnormal proteins and proteinaceous particles based on a method that utilizes catalytic propagation. Upon interaction of a sample, containing abnormal proteins or proteinaceous particles, with a peptide probe of the invention, the peptide probe undergoes conformational changes resulting in the formation of aggregates. The addition of the abnormal proteins and proteinaceous particles catalyzes the formation of the aggregates and causes further propagation of this conformational transition. The resulting aggregates are then easily detected using common analytical instrumentation and techniques.

The abnormal proteins and proteinaceous particles on which the invention focuses are proteins, protein based chemical structures such as prions and protein subunits such as peptides that are capable of conformational changes that lead to the formation of aggregates and ultimately to disease states.

Figure 7:
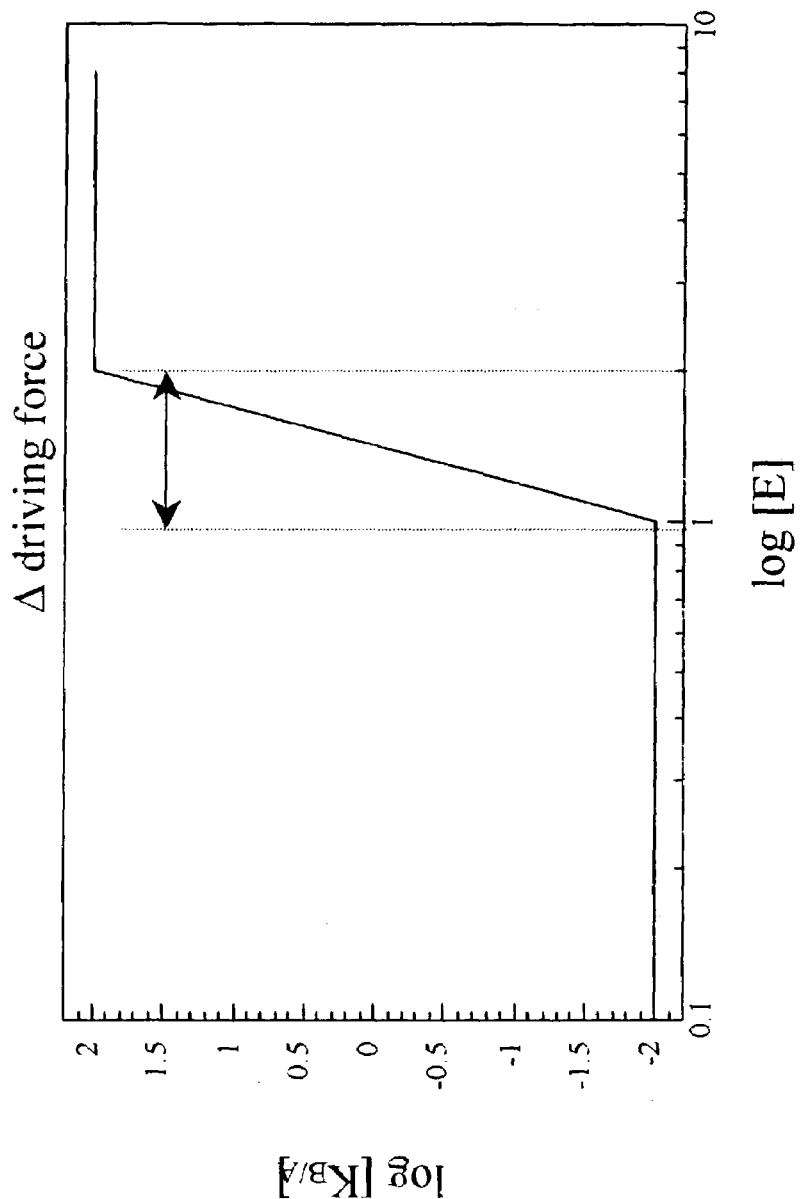
FIG. 7 is a graph of the driving force necessary to overcome the energy difference between two different conformational states.

These proteins and proteinaceous particles form aggregates by shifting from a monomeric to a multimeric state. The shift from one distinct state to the other requires a driving force that is commensurate with the energetic difference between the two conformational states as shown in FIG. 7.

A preferred example of such proteinaceous particles is that of a prion protein. Prions can exist in one of two distinct conformations characterized by having a secondary protein structure that is either predominately alpha-helical or predominately beta-sheet; where the predominately beta-sheet conformation has a much higher preference to exist in a multimeric state. As a result, predominately beta-sheet (or beta rich) secondary structure is more typical of abnormally folded or disease-causing proteinaceous particles since their preference to aggregate is likely to be disruptive in an in vivo environment.

Figure 1:
FIG. 1 is a pictoral representation of conformers of transmissible spongiform encephalopathies (TSE)

FIG. 1 shows illustrations of both the alpha-helical monomer 10 and the beta-sheet dimer 12 forms of a TSE conformer. The normal wild-type (wt) form of prion protein ($PrP^C$) prefers a monomeric state, while the abnormal, disease-causing form ($PrP^{Sc}$) more readily takes on a multimeric state.

This distinction between the secondary structure of the normal form of prion protein and the abnormal form as well as its propensity to cause aggregation is exploited in the present invention to allow detection of the abnormal form even in samples with very low levels of infectious abnormal protein.

Figure 2:
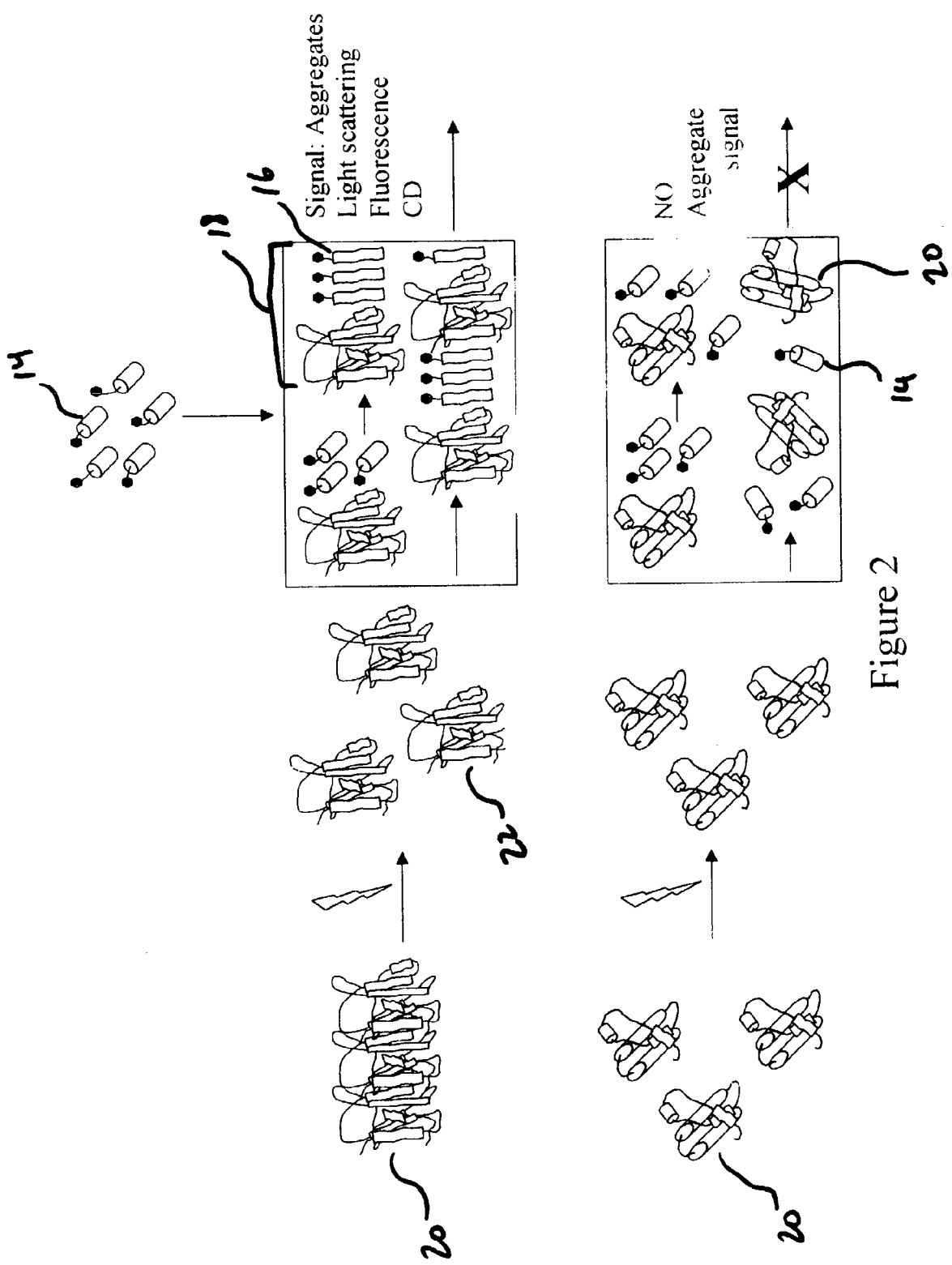
FIG. 2 is a pictoral representation of TSE protein detection schema.

The mechanism of the invention is shown in a schematic in FIG. 2. The top row of the schematic shows an example of an unknown sample of TSE protein represented as containing beta-sheets 12. The beta-sheets are then disaggregated by subjecting the sample to commonly known disaggregation methods such as sonication. This is followed by the addition of labeled peptide probes 14 which are allowed to bind to the sample 12. Presence of the beta-sheet conformation in the sample 12 induces the peptide probes to also shift to beta-sheet formation 16. In this manner the transition to beta-sheet is propagated among the peptide probes 14 thereby causing new aggregates 18 to form. The resulting transition to a predominately beta-sheet form and amplified aggregate formation can then easily be detected using common analytical techniques such as light scattering and circular dichroism (CD); and in a particularly preferred embodiment where the peptide probe is fluorescent labeled, fluorescence detection instrumentation can also be used.

The bottom row of FIG. 2 shows an alternative example in which the unknown sample of TSE protein is represented in its normal alpha-helical form 10. For consistency, the sample is subjected to the same disaggregation process described above. Upon addition of the labeled peptide probes 14, neither a transition to beta-sheet form nor binding to the unknown samples occurs. As a result, there is no aggregate fluorescence signal in the case of a labeled peptide probe as well as no detection of aggregate formation by other analytical tools. Based on this schematic, unknown samples can be tested for the presence or absence of such abnormal protein conformations or sequences.

A preferred embodiment of the invention involves the following basic procedures. Peptide probes 14 are selected in order to be added to an unknown or test sample 20 at a later stage in the process. The peptide probes 14 are preferably proteins or peptide sequences that have secondary structures of predominately alpha-helix or random coil. In a particularly preferred embodiment, the peptide probes 14 are peptide fragments consisting of a helix-loop-helix structure as found in lysine. In another particularly preferred embodiment, the peptide probes can be made of a peptide sequence chosen from wild-type (wt) TSE, from a desired species-specific TSE peptide sequence, or even from a selectively mutated TSE sequence that has been mutated in such a manner as to render it destabilized and noninfectious. Additionally, extrinsic fluors such as pyrene can be added or designed into the peptide probe to allow detection of anticipated conformational changes using common fluorescence detection techniques.

Once a peptide probe 14 is selected, it is added to a test sample 20. Prior to the addition of the peptide probe 14, however, it is preferred to have the sample 20 subjected to disaggregation techniques commonly known in the art, such as sonication. The disaggregation step allows any potentially aggregated sample material 20 to break 11 apart so that these disaggregated sample materials 22 are more free to recombine with the newly introduced peptide probes 14; thereby facilitating the anticipated catalytic propagation.

After the test sample 20 or disaggregated test sample 22 is allowed to interact with the peptide probes 14. The resulting mixture is then subjected to analytical methods commonly known in the art for the detection of aggregates and to fluorescence measurements in cases where fluorescent peptide probes 14 are used.

Unknown or test samples 20 containing any dominant beta-sheet formation characteristic of abnormally folded or disease-causing proteins results in an increase in beta-sheet formation and consequently aggregate formation in the final mixture containing both the test sample 20 and the peptide probes 14. Conversely, unknown or test samples 20 which lack a predominantly beta-sheet secondary structure will neither catalyze a transition to beta-sheet structure 16 nor will propagate the formation of aggregates 18.

One of ordinary skill in the art can appreciate that the means by which the initial conformational change can be triggered in the test samples 20 can be varied as described in the following examples. The binding of a metal ligand could direct a change in the protein scaffolding and favor aggregation. The expression or cleavage of different peptide sequences can promote advanced aggregation leading to fibril and plaque formation. Genetic point mutations can also alter the relative energy levels required of the two distinct conformations, resulting in midpoint shifts in structural transitions. Furthermore, an increase in concentration levels could be sufficient to favor the conformational transition. Regardless of the initial trigger mechanism, however, the disease process in many of the abnormal protein conformations such as in prion-related diseases always involves the catalytic propagation of the abnormal conformation, resulting in transformation of the previously normal protein.

One of ordinary skill in the art can also appreciate that there are many common protein aggregate detection techniques many of which are based on optical measurements. These optical detection techniques include, but are not limited to, light scattering, or hydrophobicity detection using extrinsic fluors such as 1-anilino-8-napthalene sulfonate (ANS) or Congo Red stain, fluorescence proximity probes on the peptide fragments, including fluorescence resonance energy transfer (FRET) & quenching of intrinsic tryptophan fluorescence through either conformational change of monomer or binding at interface in alpha-beta heterodimer; the N-terminal loop region is particularly interesting in this regard selective binding to target protein, circular dichroism (CD) monitoring of actual conformation, nuclear magnetic resonance (NMR). Other detection techniques include equilibrium ultracentrifugation or size-exclusion chromatography at the aggregation stage as well as other structural techniques. Many of these enumerated optical and structural methods are rapid, cost-effective and accurate.

Experiments were performed using model systems to show the conformational changes involved in the transition from a predominately alpha-helix to a beta-rich form. The model systems chosen used readily available, nonneurotoxic polyamino acids such as polylysine and polyglutamine. The polyamino acids were chosen because of their availability and more importantly because they are safe to handle thus eliminating the need for special handling or donning cumbersome extra protective gear.

Figure 3:
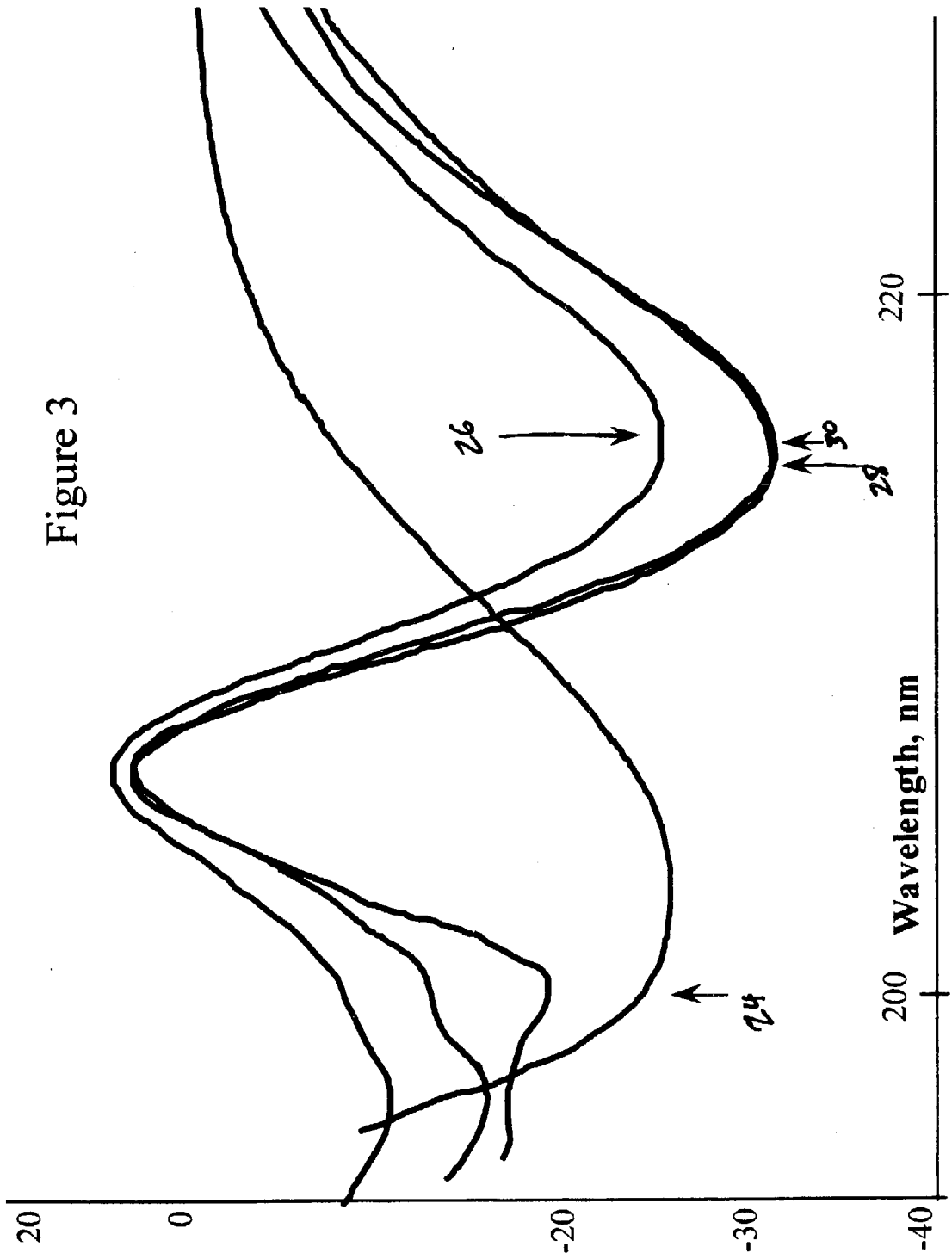
FIG. 3 is a graph showing the conformational changes associated with a poly-L-lysine test peptide using circular dichroism.

FIG. 3 shows a circular dichroism graph of experimentation with poly-L-lysine 20 micro Molar (µM) 52,000 molecular weight (MW) as a peptide probe. The resulting graphs show:

Sample 24 which was maintained at pH7, 25° C. resulting in a minimum at approximately 205 nanometers (nm) indicating random coil structure.

Sample 26 which was maintained at pH11, 50° C. resulting in a minimum at approximately 216 nanometers (nm) indicating beta-sheet structure.

Sample 28 which was a 1:1 combination of samples maintained at pH7, 25° C. and at pH11, 50° C. resulting in a minimum at approximately 216 nanometers (nm) indicating beta-sheet structure.

Sample 30 which was a 1:1 combination of samples maintained at pH7, 50° C. and at pH11, 50° C. resulting in a minimum at approximately 216 nanometers (nm) indicating beta-sheet structure.

Figure 4:
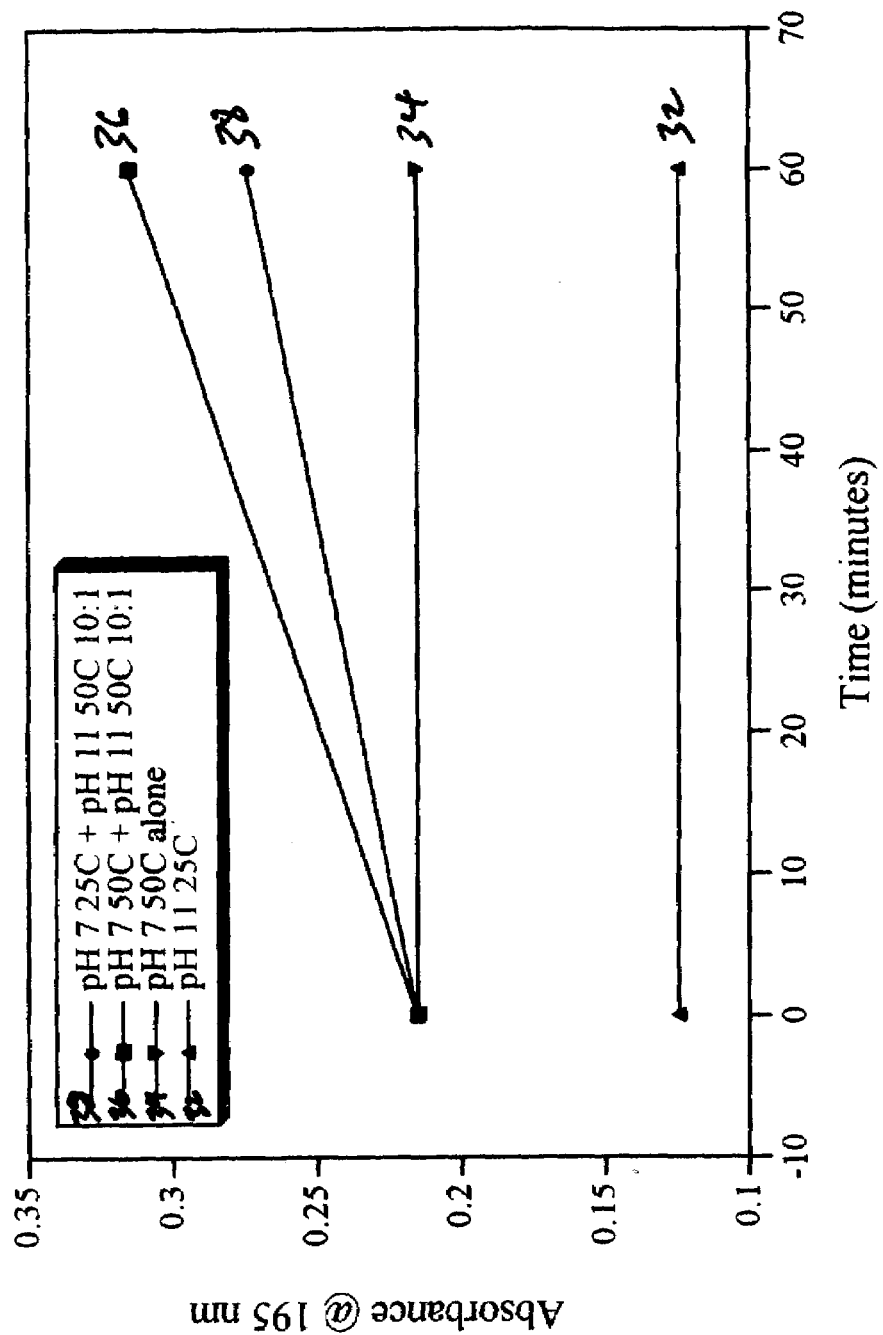
FIG. 4 is a graph comparing the circular dichroism results of the poly-L-lysine test peptide at different temperatures and pH.

FIG. 4 shows an absorbance graph of experimentation with poly-L-lysine 70 mircomolar (µM) 52,000 molecular weight (MW) as a peptide probe. The resulting graphs show:

Sample 32 which was maintained at pH 11, 25° C. resulting in a plateau at approximately 0.12 indicating predominately alpha-helical structure.

Sample 34 which was maintained at pH7, 50° C. resulting in a a plateau at approximately 0.22 indicating random coil structure.

Sample 36 which was a 10:1 combination of samples maintained at pH7, 50° C. and at pH11, 50° C. resulting in a steeper incline from approximately 0.22 to 0.33 indicating an accelerated transition from random coil to beta-sheet structure.

Sample 38 which was a 10:1 combination of samples maintained at pH7, 25° C. and at pH11, 50° C. resulting in a gradual incline from approximately 0.22 to 0.26 indicating a transition from random coil to beta-sheet structure.

FIG. 4 shows general circular dichroism results of experimentation with poly-L-lysine at varying temperatures and pH indicating its potential for transitioning from random coil to beta-sheet under the varying environmental conditions. The results indicate that both temperature and pH play an important role in the transition.

The observations based on all of the modeling experimentation described above show that the addition of a relatively small amount of beta-sheet peptide to random coil sample can result in a shift towards a beta-rich conformation and such changes can be accelerated depending on the temperature and pH environment of the samples.

Figure 6:
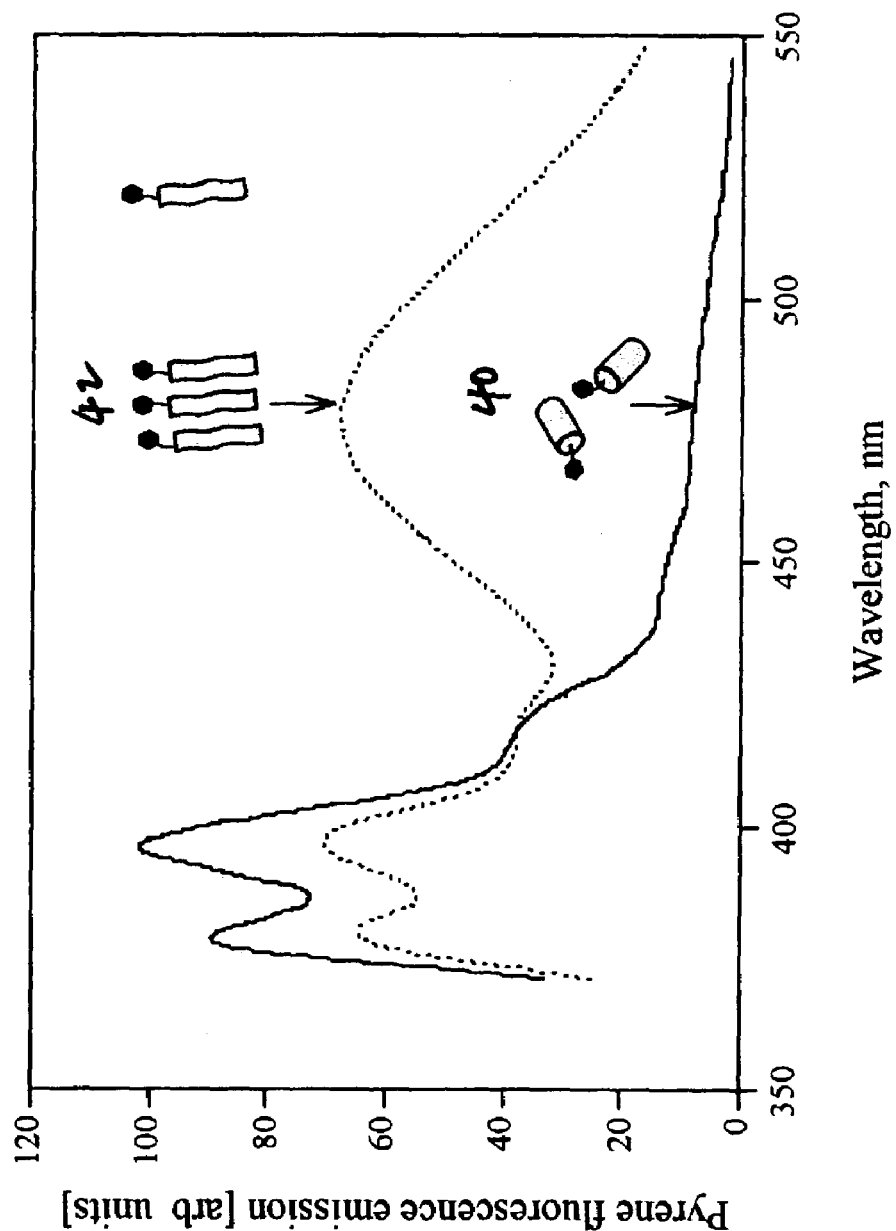
FIG. 6 is a graph of data for fluorescence resonance energy transfer (FRET) experiments for proximal and distal locations in an a-helical bundle structure undergoing conformational change.

FIG. 6 shows experimentation results using pyrene as a fluorescent probe in proximal and distal locations in an alpha helical bundle structure undergoing conformational change. The pyrene excimer formation 42 is shown at 480 nm and the spectra for a predominately alpha-helical structure 40 is contrasted as well. Those skilled in the art would appreciate that other fluorescent probes such as Fourier Transform Infrared Spectroscopy (FITC) can also be used.

A primary objective of this invention also encompasses use of the catalytic propagation of conformational change to directly correlate the measures of abnormal prion presence with levels of infectivity. For this reason we favor implementation of the invention in a manner where there is no increase in resulting infectious products as a result of the propagation. This can be achieved by placing a "break" in the links between the chain of infection, transmission and propagation of the abnormal form. Such a "break" must occur at the transitional stage between the dimer and multimer forms of the aggregate. The physical formation of the multimer form can be blocked by simply impeding the step which leads to its formation. This may be done, preferably by using a large pendant probe or by a neutral "blocker" segment, bearing in mind that probes on linkers or "tethers" are more likely to encounter each other and thus result in amplifying the signal.

Furthermore, it follows inherently in everything that is prescribed in the teachings of the provisional that in the practice of this invention, neither the peptide probe nor the final mixture is infectious—unlike all other prior art in the field of prion assay.

All of the foregoing information is found within the aforementioned provisional patent application Ser. No. 60/295,456 filed May 31, 2000 from which priority is claimed. Although not included in the provisional application, analytical methods for appraising aggregation of proteins are included in the following publications which are prior art. Freifelder, David. *Physical Biochemistry: Applications to Biochemistry and Molecular Biology*, (W. H. Freeman Press, New York, 2nd ed. 1982). Copeland, Robert. *Analytical Methods for Proteins*, (American Chemical Society Short Courses 1994). both of which are wholly incorporated herein as prior art.

Accordingly, the present invention is not limited to the specific embodiments illustrated herein. Those skilled in the art will recognize, or be able to ascertain that the embodiments identified herein and equivalents thereof require no more than routine experimentation, all of which are intended to be encompassed by claims.

Furthermore, it will be understood that the foregoing disclosure is intended to be merely exemplary, and not to limit the scope of the invention—which is to be determined by reference to the appended claims.

What is claimed is:

1. A method for detecting, in body fluids, misfolded proteinaceous particles comprising a predominantly beta-sheet secondary structure, said method comprising:
   (a) obtaining a test specimen comprising body fluids;
   (b) adding a propagation catalyst to the test specimen, thereby forming a mixture, wherein: (i) the propagation catalyst is a peptide; (ii) the peptide has a predominantly alpha-helix and/or random coil secondary structure that interacts with misfolded proteinaceous particles, and (iii) the peptide undergoes a conformational shift that results in a decrease in alpha-helix and/or random coil secondary structure and an increase in beta-sheet secondary structure upon contact with misfolded proteinaceous particles or upon contact with another such propagation catalyst that has undergone such a conformational shift;
   (c) allowing the propagation catalyst and any misfolded proteinaceous particles in the test specimen to interact; and
   (d) detecting any increase in beta-sheet secondary structure in the mixture, the increase being due, at least in part, to an increase in beta-sheet secondary structure of the propagation catalyst, wherein any such increase indicates the presence of misfolded proteinaceous particles in the test specimen.

2. The method of claim 1, wherein said obtaining step does not include physically sacrificing a subject from which the test specimen is obtained.

3. The method of claim 1, wherein said obtaining step comprises drawing body fluids but does not comprise biopsy of tissues or organs.

4. The method of claim 1, wherein said propagation catalyst is an optically labeled peptide.

5. The method of claim 1, wherein said body fluids comprise fluids present in animals substantially in fluid form.

6. The method of claim 5, wherein said body fluids comprise diluent in combination with fluids present in animals substantially in fluid form.

7. The method of claim 5, wherein said body fluids comprise blood.

8. The method of claim 5, wherein said body fluids comprise cerebral spinal fluid.

9. The method of claim 5, wherein said body fluids comprise lymph.

10. The method of claim 1, wherein the propagation catalyst is not infectious and the step of adding the propagation catalyst to the specimen is not infectiously hazardous to performers of the step.

11. The method of claim 1, wherein the propagation catalyst is not infectious and the step of detecting any increase in beta-sheet secondary structure in the mixture is not infectiously hazardous to performers of the step.

12. The method of claim 1, wherein the detecting step comprises taking optical measurements or structural measurements.

13. An in vitro method of detecting the presence of a misfolded form of a prion protein ($PrP^{SC}$) comprising a predominantly beta-sheet secondary structure in a sample, said method comprising:
   (a) obtaining a sample comprising body fluids;
   (b) adding a propagation catalyst to the sample, wherein:
      (i) the propagation catalyst is a peptide; (ii) the peptide has a predominantly alpha-helix and/or random coil secondary structure that interacts with a $PrP^{SC}$, and (iii) the peptide undergoes a conformational shift that results in a decrease in alpha-helix and/or random coil secondary structure and an increase in beta-sheet secondary structure upon contact with misfolded $PrP^{SC}$ comprising a predominantly beta-sheet secondary structure or upon contact with another such propagation catalyst that has undergone such a conformational shift;
   (c) allowing the catalyst and any misfolded $PrP^{SC}$ present in the sample to interact; and
   (d) detecting any increase in beta-sheet secondary structure in the mixture, the increase being due, at least in part, to an increase in beta-sheet secondary structure of the propagation catalyst, wherein any such increase indicates the presence of misfolded $PrP^{SC}$ in the sample.

14. The method of claim 13, wherein the propagation catalyst is an optically labeled peptide.

15. The method of claim 14, wherein the detecting step comprises taking optical measurements.

16. The method of claim 15, wherein the propagation catalyst comprises a fluorescent label and the detecting step comprises detecting fluorescence of the propagation catalyst.

17. The method of claim 13, wherein the detecting step comprises taking structural measurements, using an analytical technique selected from light scattering and circular dichroism, or a combination thereof.

18. The method of claim 13, wherein the propagation catalyst comprises an amino acid sequence selected from the group consisting of a polylysine sequence, a polyglutamine sequence, and a sequence from a $PrP^{SC}$.

19. The method of claim 13, wherein the method further comprises, prior to the step of adding the propagation catalyst to the sample, the step of subjecting the sample to a disaggregation technique.

20. The method of claim 13, wherein the bodily fluids are obtained from a living animal.

21. The method of claim 13, wherein the body fluids comprise blood.

22. The method of claim 13, wherein the body fluids comprise cerebral spinal fluid.

23. The method of claim 13, wherein the body fluids comprise lymph.

24. The method of claim 13, wherein the propagation catalyst is not infectious.

25. The method of claim 24, wherein the step of adding the propagation catalyst to the sample is not infectiously hazardous to performers of the step.

26. The method of claim 24, wherein the step of detecting any increase in beta-sheet secondary structure in the mixture is not infectiously hazardous to performers of the step.

27. The method of claim 13, wherein the $PrP^{SC}$ is associated with transmissible spongiform encephalopathy (TSE).

28. The method of claim 27, wherein the propagation catalyst comprises a polylysine amino acid sequence.

29. The method of claim 13, wherein the $PrP^{SC}$ is associated with Creutzfeldt-Jakob syndrome.

30. The method of claim 13, wherein the $PrP^{SC}$ is associated with scrapie.

31. The method of claim 4, wherein the propagation catalyst comprises a fluorescent label and the detecting step comprises detecting fluorescence of the propagation catalyst.

32. The method of claim 1, wherein the detecting step comprises using an analytical technique selected from light scattering and circular dichroism.

33. The method of claim 1, wherein the propagation catalyst comprises an amino acid sequence selected from the group consisting of a polylysine sequence, a polyglutamine sequence, and a sequence from the proteinaceous particle.

34. The method of claim 1, wherein the method further comprises, prior to the step of adding the propagation catalyst to the specimen, the step of subjecting the sample to a disaggregation technique.

35. The method of claim 5, wherein the bodily fluids are obtained from a living animal.

36. The method of claim 1, wherein the proteinaceous particle is a disease-associated protein.

* * * * *